United States Patent [19]

Olah

[11] Patent Number: 4,547,606
[45] Date of Patent: Oct. 15, 1985

[54] SELECTIVE ISOMERIZATION OF DI-ISOPROPYL BENZENE TO META-DI-ISOPROPYL BENZENE

[75] Inventor: George A. Olah, Beverly Hills, Calif.

[73] Assignee: PCUK Produits Chimiques Ugine Kuhlmann, Courbevie, France

[21] Appl. No.: 576,802

[22] Filed: Feb. 6, 1984

Related U.S. Application Data

[60] Continuation of Ser. No. 348,956, Feb. 16, 1982, abandoned, which is a continuation-in-part of Ser. No. 211,775, Dec. 1, 1980, abandoned, which is a division of Ser. No. 130,401, Mar. 14, 1980, abandoned.

[51] Int. Cl.$^4$ ............................................. C07C 5/22
[52] U.S. Cl. ................................................. 585/477
[58] Field of Search ........................................ 585/477

[56] References Cited

U.S. PATENT DOCUMENTS

| | | | |
|---|---|---|---|
| 2,741,647 | 4/1956 | McCauley et al. | 585/477 |
| 2,770,662 | 11/1956 | McCauley et al. | 585/477 |
| 3,678,120 | 7/1972 | Bloch | 585/464 |
| 3,766,286 | 10/1973 | Olah | 585/477 |
| 4,065,405 | 12/1977 | Hulme | 585/464 |

FOREIGN PATENT DOCUMENTS 816984  7/1959  United Kingdom ............... 585/477

*Primary Examiner*—Curtis R. Davis

[57] ABSTRACT

Resorcinol is prepared in high yield and purity by an improved process through superacid (such as perfluorinated alkanesulfonic acids of one to eighteen carbon atoms or polymeric perfluorinated resinsulfonic acids, such as acidified Nafion-H, catalyzed cleavage rearrangement reaction of meta-bis(2-hydroperoxy-2-propyl)benzene (meta-diisopropylbenzene dihydroperoxide). Part of the process is the preparation of needed meta-diisopropylbenzene in high purity (98–100%) substantially free of other isomers by treating any mixture of diisopropylbenzenes with an excess of anhydrous hydrogen fluoride or a perfluorinated alkanesulfonic acid of one to eighteen carbon atoms and a Lewis acid fluoride, or by alkylating (transalkylating) cumene with a propyl alkylating agent in the aforementioned superacid systems.

13 Claims, No Drawings

SELECTIVE ISOMERIZATION OF DI-ISOPROPYL BENZENE TO META-DI-ISOPROPYL BENZENE

RELATED APPLICATIONS

This is a continuation of application Ser. No. 348,956, filed Feb. 16, 1982, abandoned, which is a continuation-in-part of application Ser. No. 211,775 filed Dec. 1, 1980, now abandoned which is in turn a division of Ser. No. 130,401 filed Mar. 14, 1980 now abandoned.

TECHNICAL FIELD

Resorcinol is prepared in high yield and purity by an improved process through superacid (such as perfluorinated alkanesulfonic acids of one to eighteen carbon atoms or polymeric perfluorinated resinsulfonic acids, such as Nafion-H catalyzed cleavage-rearrangement reaction of meta-bis(2-hydroperoxy-2-propyl)-benzene (meta-diisopropylbenzene dihydroperoxide). Part of the process is the preparation of needed meta-diisopropylbenzene in high purity (98-100%) substantially free of other isomers by treating any mixture of diisopropylbenzene isomers with an excess of anhydrous hydrogen fluoride or a perfluorinated alkanesulfonic acid of one to eighteen carbon atoms and a Lewis acid fluoride or by alkylating (transalkylating) cumene with a propyl alkylating agent in the aforementioned superacid systems.

BACKGROUND ART

Resorcinol (meta-dihydroxybenzene) is an industrial chemical of substantial utility. Its preparation is usually carried out through the high temperature (about 300° C.) alkali fusion of meta-benzenedisulfonic acid. For chemical, energy, as well as environmental reasons, this process is disadvantageous. Efforts were made to apply the Hock reaction for the preparation of phenol from isopropylbenzene, to that of resorcinol from meta-diisopropylbenzene through the dihydroperoxide of meta-diisopropylbenzene (see, for example, U.S. Pat. Nos. 2,736,753 and 2,862,857; German Offen. Nos. 2,646,032 and 2,737,302; Japan Kokai Nos. 78 02,434; 78 02,436; 78 53,626 and 79 03,022; British Pat. Nos. 819,450; 857,113; 873,676 and 982,514; and Netherlands Pat. No. 6,400,270). However, the presence of two hydroperoxide groups existing simultaneously in the intermediate dihydroperoxide can result, under the usual conditions of the Hock reaction using sulfuric acid or silica-alumina (titania) catalysts, in the formation of a significantly increased number of by-products, and, thus, lower yields than in the case of cumene hydroperoxide (see Weissermel and Arpe, "Industrial Organic Chemistry", Verlag Chemie, Weinheim (Germany), New York, 1978, pp. 317-318).

DISCLOSURE OF THE INVENTION

The present invention relates to the improved superacid catalyzed preparation of resorcinol from meta-diisopropylbenzene through its dihydroperoxide, as well as to preparation of the needed meta-diisopropylbenzene in high purity substantially free of other isomers.

BEST MODES FOR CARRYING OUT THE INVENTION

It was discovered that meta-diisopropylbenzene dihydroperoxide prepared by known methods, such as the liquid phase oxidation of meta-diisopropylbenzene with oxygen or air in the presence of Cu, Mn or Co salts, HBr or pyridine—HBr (or other tertiary amine—HBr salts) and similar catalysts, can be cleanly converted and in high yield (>90%), via its Hock-reaction, to resorcinol, when treated with a superacid catalyst, such as a perfluorinated sulfonic acid of one to eighteen carbon atoms or related polymeric perfluorinated resinsulfonic acids, such as acidified Nafion-H, and the like. The reaction is generally carried out in solvents, such as benzene, toluene, cumene, meta-diisopropylbenzene, acetone, sulfolane, and the like, or mixtures thereof, at temperatures between −50° and 150° C., with the superacid catalyst dissolved or dispersed in the solvent system.

The polymeric perfluorinated resinsulfonic acids (Nafion-H) can be prepared from commercially available Nafion-K (DuPont) ion-membrane resin by acidification. This perfluorinated resinsulfonic acid comprises a fluorinated polymer having sulfonic acid groups in the amount of about 0.01 to 5 mequiv/gram catalyst. The polymer catalyst contains a repeating structure, which can be depicted as:

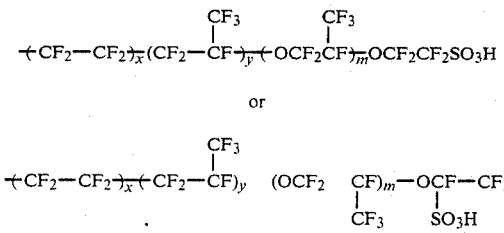

where the ratio of x over y varies from about 2 to about 50, and m is 1 or 2. This polymer structure is available commercially under the tradename Nafion resin from DuPont. Polymer catalysts of the above structure can be prepared in various ways. One method, disclosed in Conolly et al. U.S. Pat. No. 3,282,875 and Cavanaugh et al. U.S. Pat. No. 3,882,093 comprises polymerizing the corresponding perfluorinated vinyl compounds. It is also possible to prepare polymer catalysts according to U.S. Pat. No. 4,041,090 by copolymerizing the corresponding perfluorinated vinyl ethers with perfluoroethylene and/or perfluoroalpha-olefins. The specific fluorinated repeating structure depicted above is not critical but perfluorinated is preferred. The Nafion ion exchange resins can be acidified in various known manners such as set forth in Example 2 below.

The conversion can also be advantageously carried out in situ when reacting the corresponding meta-bis(2-hydroxy-2-propyl)benzene with hydrogen peroxide over a perfluorinated sulfonic acid or perfluorinated resinsulfonic acid catalyst, while azeotropically distilling off water and acetone formed from the reaction mixture.

Without limiting in any way the scope of the invention or speculating on the effectiveness of superacidic catalysts, it is pointed out that these catalysts are capable of substantially speeding up the rate of the cleavage-rearrangement reaction of meta-diisopropylbenzene dihydroperoxide, which otherwise is markedly slower than that of the related reaction of cumene hydroperoxide or para-diisopropylbenzene dihydroperoxide, resulting in formation of significantly increased amounts of by-products, which tend to decrease the yield of conversion.

Superacids are those acids having an acidity function below $H_o = -11$ on the logarithmic Hammett $H_o$, acidity function scale. For example, 100% sulfuric acid has an $H_o$ function of $-11$, while superacids would have $H_o$ values of $-14$, $-20$, etc.

It is a significant aspect of the invention to obtain the needed starting material, i.e. meta-diisopropylbenzene in high isomeric purity. Practical methods known for preparation of this compound consist of isopropylation of cumene, giving isomeric mixtures with the ortho and para isomers predominating. Subsequent acid catalyzed isomerization, using usual Friedel-Crafts conditions or solid acid catalysts, increase the amount of meta-isomer up to about 60% of the mixture, but still necessitate separation of the isomers which, due to their close boiling ranges, can generally not be effected by simple distillation alone and thus separation of the isomers is difficult to achieve and expensive.

The thermodynamic mixture of isomeric diisopropylbenzenes contains only about 66% of the meta-isomer. The aluminum chloride catalyzed Friedel-Crafts isomerization of diisopropylbenzenes was studied by Olah, Meyer and Overchuck (*J. Org. Chem.*, 29, 2315 (1964) and was shown to give an equilibrium composition containing 66% of meta and 34% para isomer, accompanied also by significant disproportionation giving cumene and triisopropylbenzenes.

It has now been discovered that when carrying out the isomerization of mixed diisopropylbenzenes in the presence of an excess of anhydrous hydrogen fluoride, or a perfluorinated alkanesulfonic acid of one to eighteen carbon atoms and a Lewis acid fluoride, such as boron trifluoride, phosphorus pentafluoride, antimony pentafluoride, arsenic pentafluoride, tantalum pentafluoride, niobium pentafluoride and the like, at temperatures between $-50°$ and $200°$ C., preferentially between $0°$ and $50°$ C., the results is the formation of practically pure (99 to 100%) meta-diisopropylbenzene. The isomerization is accompanied by disproportionation to cumene and triisopropylbenzene (mainly, the 1,3,5-isomer). The latter reaction can be, however, suppressed when adding (recycling) 1,3,5-triisopropylbenzene to transalkylate cumene. This transalkylation reaction can itself be used to prepare meta-diisopropylbenzene in high purity (99+%) when carrying out the process, for example, in HF—$BF_3$ at $-20°$ C. to $0°$ C.

Superacid systems form protonated complexes with aromatics, i.e., arenium ions. In case of diisopropylbenzenes, the complex formed from the meta isomer is the most stable. Thus, the superacid systems tend to selectively extract the meta isomer and allow a selective conversion of all isomers into the meta product. Such isomerization shifted beyond the thermodynamic equilibrium of the neutral hydrocarbon isomers was known previously only for methylbenzenes (McCaulay and Lien, *J. Am. Chem. Soc.*, 74, 6246 (1952), but not for isopropylbenzenes. Methyl-benzenes isomerize intramolecularly, whereas isopropylbenzenes tend to isomerize by intermolecular process. Thus, no extrapolation is possible from methylbenzenes to isopropylbenzenes, which are also expected to significantly disproportionate, nor were any results predictable or expected concerning the treatment of diisopropyl benzenes in superacids.

The alkylation [transalkylation] of cumene with a propylene alkylating agent such as propylene, isopropyl halides or isopropyl alcohol in anhydrous HF or perfluoroalkanesulfonic acid of one to eighteen carbon atoms in the presence of the aforementioned Lewis acid fluoride catalysts also results in the substantially exclusive formation of meta-diisopropylbenzene.

Meta-diisopropylbenzene (in practically 100% purity) can also be obtained by carrying out the isopropylation of cumene by transalkylation with triisopropylbenzene in the same superacid systems. These conditions also tend to minimize disproportionation of formed meta-diisopropylbenzenes.

The scope of the invention is further described in connection with the following examples, which are set forth for purposes of illustration only and are not to be construed as limiting the scope of the invention in any manner.

EXAMPLE 1

5 g of perfluorinated decanesulfonic acid (PDSA) is dissolved (dispersed) in a mixture of 100 ml acetone and 100 ml toluene, heated to reflux, and 23 g (0.05 mol) meta-diisopropylbenzene dihydroperoxide (neat or as a solution in diisopropylbenzene) is then added continuously with good stirring. After addition is completed, stirring is continued for an hour. Resorcinol is either extracted from the reaction mixture with a suitable solvent, such as diisopropyl ether or is separated by vacuum distillation, giving 9.3 g (85%) of resorcinol in 97% purity.

EXAMPLE 2

Reaction carried out as in Example 1, but using 3 g Nafion-H as a catalyst dispersed in 150 ml sulfolane as solvent, at a temperature of 130° to 150° C. Nafion-H is prepared from commercial (DuPont) potassium salt of the resin (Nafion-K) by acidification with 20 to 30% nitric acid, stirring at 20° to 50° C. for four hours, filtering the resin acid, washing it acid free with water and subsequently drying it in a vacuum oven at 105°–110° C. for eight hours. An 87% yield of resorcinol in 96% purity is obtained.

EXAMPLE 3

3 g of trifluoromethanesulfonic acid is dissolved in 100 g of sulfolane. The solution is heated to around 100° C. and about 30% solution of 12 g (0.1 mol) of meta-diisopropylbenzene dihydroperoxide in meta-diisopropylbenzene is added continuously to the stirred solution, while distilling off formed acetone from the reaction mixture. Isolation of resorcinol is effected as in Example 1. A 92% yield of resorcinol is obtained with 98% purity.

EXAMPLE 4

19.4 g (0.1 mol) of meta-bis(2-hydroxy-2-propyl)benzene is dissolved in 150 ml of dioxane and 5 g of Nafion-H catalyst (as prepared in Example 2) is added to the stirred mixture and heated to reflux. A solution of 8 g (0.2 mol) 90% hydrogen peroxide in 50 ml dioxane is then slowly added with good stirring during a period of two hours, while stirring is continued. The water and acetone formed is continuously distilled off during the reaction. Workup and isolation of resorcinol, after filtering off the solid superacid catalysts, is as in Example 1. Yield 56%, purity 98%.

EXAMPLE 5

A commercial mixture of 16 g (0.1 mol) diisopropylbenzene containing about 60% of the para and 40% of the ortho isomer, is dissolved in 150 ml of anhydrous hydrogen fluoride. The reaction mixture is cooled to $-20°$ to $0°$ and saturated, while stirred, with boron trifluoride. After stirring at this temperature for 30 min., the temperature is raised and HF and $BF_3$ is distilled off, (which can be reused). After washing, neutralization and drying, the organic layer is separated, distilled and analyzed by gas liquid chromatography. The diisopropylbenzene fraction consists of 99% meta-diisopropylbenzene and 1% para-diisopropylbenzene. Cumene and 1,3,5-triisopropylbenzene are also formed, as products of disproportionation, amounting to about 20%.

EXAMPLE 6

12 g (0.1 mol) cumene and 10 g (0.05 mol) triisopropylbenzene are dissolved in 150 ml of anhydrous hydrogen fluoride at a temperature between $-20°$ and $0°$. While stirring the reaction mixture at this temperature, it is saturated with boron trifluoride and stirring is continued for two hours. After workup, as in Example 5, 36% diisopropylbenzene was obtained, comprised of 99.2% of the meta and 0.8% of the para isomer.

EXAMPLE 7

12 g (0.1 mol) cumene is dissolved in 150 ml anhydrous hydrogen fluoride and while keeping the stirred solution at $-20°$ C. to $0°$ C., 0.05 mol of propylene is introduced and stirring continued for 15 min. The reaction mixture is then saturated with boron trifluoride and stirring continued for another 15 min. After workup, 41% diisopropylbenzene was obtained, comprised of 99.6% of meta and 0.4% para isomer, together with about 15% 1,3,5-triisopropylbenzene, which can be recycled under conditions of Example 6 to produce more meta-diisopropylbenzene.

While the invention has been described in connection with preferred embodiments, it is not intended to limit the invention to the particular forms set forth, but, on the contrary, it is intended to cover such alternatives, modifications, and equivalents as may be included within the spirit and scope of the invention.

I claim:

1. A process for producing a substantially pure meta-diisopropyl benzene isomer which comprises reacting a mixture of diisopropyl benzene isomers said mixture being other than a substantially pure meta-diisopropyl benzene isomer with anhydrous hydrogen fluoride in the presence of a Lewis acid fluoride catalyst at a temperature between about $-50°$ and $200°$ C. to produce said meta-diisopropyl benzene isomer.

2. The process of claim 1 in which the Lewis acid fluoride catalyst is boron trifluoride, phosphorous pentafluoride, arsenic pentafluoride, antimony pentafluoride, tantalum pentafluoride or niobium pentafluoride.

3. The process of claim 2 in which the isomerization reaction is performed at temperatures between about $0°$ and $50°$ C.

4. A process for preparing a substantially pure meta-diisopropyl benzene isomer which comprises reacting a mixture of diisopropyl benzene isomers, said mixture being other than a substantially pure meta-diisopropyl benzene isomer, with a perfluorinated alkanesulfonic acid of one to eighteen carbon atoms in the presence of a Lewis acid fluoride catalyst at a temperature between about $-50°$ and $200°$ C. to produce said meta-diisopropyl benzene isomer.

5. The process of claim 4 in which said Lewis acid fluoride catalyst is boron trifluoride, phosphorous pentafluoride, arsenic pentafluoride, antimony pentafluoride, tantalum pentafluoride, or niobium pentafluoride.

6. The process of claim 4 in which the isomerization reaction is performed at temperatures between about $0°$ and $50°$ C.

7. A process for producing a substantially pure meta-diisopropyl benzene isomer from a mixture of various diisopropyl benzene isomers, said mixture being other than a substantially pure meta-diisopropyl benzene isomer, which comprises adding an excess of hydrogen fluoride to said mixture at a temperature range of $-50°$ to $200°$ C. and subseqently adding a boron trifluoride catalyst to produce said meta-diisopropyl benzene isomer.

8. The process of claim 7 in which the isomerization reaction is performed at temperatures between about $0°$ and $50°$ C.

9. The process of claim 5 in which the isomerization reaction is performed at temperatures between about $0°$ and $50°$ C.

10. The process according to claim 1 wherein said mixture of diisopuopyl benzene isomers isomerize intramolecularly with less than about 20% disproportionation.

11. The process according to claim 4 wherein said mixture of diisopuopyl benzene isomers isomerize intramolecularly with less than about 20% disproportionation.

12. The process according to claim 7 wherein said mixture of diisopuopyl benzene isomers isomerize intramolecularly with less than about 20% disproportionation.

13. The process of claim 1 in which the isomerization reaction is performed at temperatures between about $0°$ and $50°$ C.

* * * * *